United States Patent
Morrison et al.

(10) Patent No.: US 10,927,395 B2
(45) Date of Patent: Feb. 23, 2021

(54) METHOD FOR USING ELECTROCHEMICAL BIOREACTOR MODULE WITH RECOVERY OF COFACTOR

(71) Applicant: BIOCHEMINSIGHTS, INC., Malvern, PA (US)

(72) Inventors: Clifford S. Morrison, Malvern, PA (US); William B. Armiger, Malvern, PA (US); David R. Dodds, Manlius, NY (US); Mattheos Koffas, Malvern, PA (US)

(73) Assignee: Biocheminsights, Inc., Malvern, PA (US)

( * ) Notice: Subject to any disclaimer, the term of this patent is extended or adjusted under 35 U.S.C. 154(b) by 131 days.

(21) Appl. No.: 16/084,579

(22) PCT Filed: Mar. 14, 2017

(86) PCT No.: PCT/US2017/022241
§ 371 (c)(1),
(2) Date: Sep. 13, 2018

(87) PCT Pub. No.: WO2017/160793
PCT Pub. Date: Sep. 21, 2017

(65) Prior Publication Data
US 2019/0078127 A1     Mar. 14, 2019

Related U.S. Application Data

(60) Provisional application No. 62/308,175, filed on Mar. 14, 2016.

(51) Int. Cl.
| | |
|---|---|
| C12P 19/36 | (2006.01) |
| C07H 1/00 | (2006.01) |
| C12N 9/02 | (2006.01) |
| C07H 21/00 | (2006.01) |
| A61K 31/7084 | (2006.01) |
| C07H 19/207 | (2006.01) |
| C12N 9/04 | (2006.01) |
| C12P 19/32 | (2006.01) |
| C12R 1/11 | (2006.01) |
| C12R 1/125 | (2006.01) |
| C12R 1/15 | (2006.01) |
| C12R 1/19 | (2006.01) |
| C12R 1/84 | (2006.01) |
| C12R 1/865 | (2006.01) |
| H01M 8/16 | (2006.01) |

(52) U.S. Cl.
CPC .......... *C12P 19/36* (2013.01); *A61K 31/7084* (2013.01); *C07H 1/00* (2013.01); *C07H 19/207* (2013.01); *C07H 21/00* (2013.01); *C12N 9/0006* (2013.01); *C12N 9/0008* (2013.01); *C12N 9/0036* (2013.01); *C12N 9/0059* (2013.01); *C12N 9/0069* (2013.01); *C12N 9/0071* (2013.01); *C12P 19/32* (2013.01); *C12R 1/11* (2013.01); *C12R 1/125* (2013.01); *C12R 1/15* (2013.01); *C12R 1/19* (2013.01); *C12R 1/84* (2013.01); *C12R 1/865* (2013.01); *C12Y 110/03001* (2013.01); *C12Y 101/01* (2013.01); *C12Y 103/01* (2013.01); *C12Y 113/11001* (2013.01); *C12Y 114/11* (2013.01); *H01M 8/16* (2013.01); *Y02E 60/50* (2013.01)

(58) Field of Classification Search
CPC ...... C12N 9/0016; C12N 9/001; C12N 9/002; C12N 9/0036; C12N 9/0042; C12N 9/0073; C12Q 1/26; C12Y 106/03; C12Y 106/00; H01M 8/16
See application file for complete search history.

(56) References Cited

U.S. PATENT DOCUMENTS

| | | |
|---|---|---|
| 6,270,649 B1 | 8/2001 | Zeikus et al. |
| 2005/0287399 A1 | 12/2005 | Ladisch |
| 2015/0228996 A1 | 8/2015 | Armiger et al. |

FOREIGN PATENT DOCUMENTS

| | | |
|---|---|---|
| CA | 1207691 A | 7/1986 |

OTHER PUBLICATIONS

Beaupre et al., "Renalase is an Alpha-NAD(P)H Oxidase/Anomerase", Journal of the American Chemical Society, vol. 135; Aug. 21, 2013, pp. 13980-13987.
Chakraverty et al., "1.6 DPNH, An Enzymatically Active Form of Reduced DPN", Biochemical and Biophysical Research Communications, vol. 15, No. 3, 1964, pp. 262-268.
Moran et al., "The enzyme: Renalase", Archives of Biochemistry and Biophysics, vol. 632, Oct. 15, 2017 (Oct. 15, 2017), pp. 66-76.
International Search Report in International Application No. PCT/US2017/022241 dated May 24, 2017.
Extended European Search Report for EP Application No. 17767305 dated Jul. 9, 2019.

*Primary Examiner* — Thane Underdahl
(74) *Attorney, Agent, or Firm* — Greenberg Traurig, LLP; Fang Xie

(57) ABSTRACT

Provided herein a re composition and process for using an electrochemical device for the reduction of the oxidized state of phosphorylated or non-phosphorylated nicotinamide adenine dinucleotide to the reduced state in which unwanted products of the electrochemical reduction are recovered as the oxidized state of the phosphorylated or non-phosphorylated nicotinamide adenine dinucleotide and returned to the electrochemical device for reduction.

20 Claims, 1 Drawing Sheet

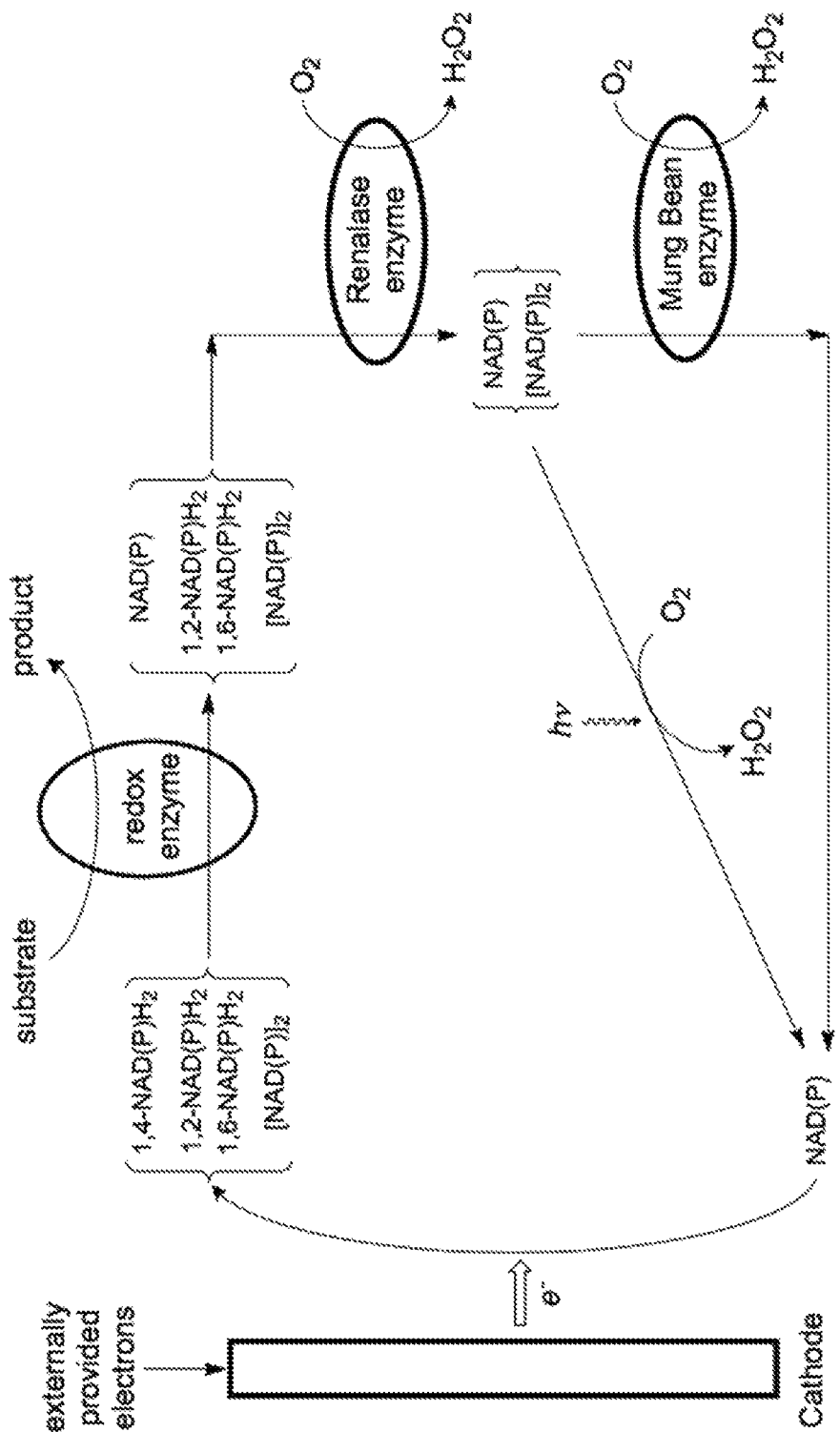

METHOD FOR USING ELECTROCHEMICAL BIOREACTOR MODULE WITH RECOVERY OF COFACTOR

CROSS REFERENCE TO RELATED APPLICATIONS

This application is a U.S. National Phase application under 35 U.S.C. 371 of International Application No. PCT/US2017/022241, filed Mar. 14, 2017, which claims priority to and the benefit of U.S. Provisional Application No. 62/308,175 filed Mar. 14, 2016, the disclosure of each of which is incorporated herein by reference in its entirety.

TECHNICAL FIELD

The present disclosure relates generally to the use of biologically mediated reactions that alter the oxidation state of compounds, and specifically the oxidation state of carbon atoms in a given chemical compound.

More specifically, the present disclosure relates to an improved method of utilizing the Electrochemical Bioreactor Module (EBM) in which undesired forms of nicotinamide adenine dinucleotide cofactor which are produced during the electrochemical reduction of the oxidized form of the nicotinamide adenine dinucleotide cofactor are recovered for recycling through the EBM.

BACKGROUND

The use of enzymes which perform a reduction, and are capable of reducing a provided substrate to a desired reduced product, has been widely reported. (Dodds et al, J. Am. Chem. Soc., (1988) 110(2), 577-583; Dodds et al, Proceedings Chiral Europe'95. London, (1995), 55-62; A. Liese et al, Appl Microbiol Biotechnol (2007) 76:237-248; Liese, A.; 2nd ed. Enzyme Catalysis in Organic Synthesis, (2002), 3, 1419-1459; Kula, M. R.; Kragl, U. Stereoselect. Biocatal. (2000), 839-866; Chartrain, M.; Greasham, R.; Moore, J.; Reider, P.; Robinson, D.; Buckland, B. J. Mol. Catal. B: Enzym. (2001), 11, 503-512; Patel, R. N. Enzyme Microb. Technol. (2002), 31, 804-826; Patel, R. N. Adv. Appl. Microbiol. (2000), 47, 33-78; Patel, R. N.; Hanson, R. L.; Banerjee, A.; Szarka, J. Am. Oil Chem. Soc. (1997), 74, 1345-1360; Hummel, W. Adv. Biochem. Eng. Biotechnol. (1997), 58, 145-184; Whitesides et al, Appl. Biochem. and Biotech. (1987) 14, 147-197; Whitesides et al, Biotechnology and Genetic Engineering Reviews, Vol. 6. September 1988).

To accomplish such a reduction of a provided substrate, electrons must be provided to the reaction. In biological systems, both in vivo and in vitro, these electrons, generally called "reducing eauivalents", are provided by small molecules generally termed "cofactors". The most common cofactor is nicotinamide adenine dinucleotide, NAD. A phosphorylated form of the cofactor also exists, and both forms provide reducing equivalents to the enzymes that catalyze reactions requiring reducing equivalents.

The nicotinamide adenine dinucleotide cofactors exist in an oxidized state and in a reduced state, and these are respectively abbreviated as NAD(P)+ and NAD(P)H in the open literature. However, these abbreviations will be avoided here.

Most generally, the enzymes accepting reducing equivalents from the reduced state of the nicotinamide adenine dinucleotide cofactors are termed "oxidoreductases" and are classified by the Nomenclature Committee of the International Union of Biochemistry and Molecular Biology as EC1.n.n.n. Of particular interest are the enzymes generally termed "dehydrogenases" or "ketoreductases" in the classes EC 1.1.n.n and EC 1.2.n.n, as well as those termed "monooxygenases" in the classes EC1.13.n.n and EC.1.14.n.n. This last group of enzymes are also termed "P450" enzymes or "CYP" enzymes.

When performing reactions catalyzed by such enzymes using micro-organisms growing on a carbon source such as a carbohydrate, the reducing equivalents are generated by oxidizing a portion of the carbohydrate to $CO_2$, that is, some of the carbohydrate provided to the micro-organism is sacrificially oxidized in order to provide electrons for the micro-organism to use in various metabolic processes. While the resulting electrons are desirable and useful to the microorganism, the carbon atoms sacrificed by oxidation to $CO_2$ are lost. It is also possible to provide carbon sources other than carbohydrates that are also sacrificed to produce the desired reducing equivalents. It will be clear that while such an in vivo process may perform the desired reaction catalyzed by the oxidoreductase enzyme, recovering the desired product from the milieu of the in vivo system, e.g. a fermentation broth, can be difficult. It is thus advantageous to utilize an in vitro system for performing the desired reaction.

It is possible to isolate the needed oxidoreductase enzyme and use it to catalyze reactions in vitro. Significantly improved chemical processes could be achieved by an in vitro system which allows the use of the plethora of oxidoreductase enzymes in processes resembling standard catalytic chemical processes. Such systems avoid the issues of recovering the desired product of the reaction from fermentation broths, and can provide further advantages by allowing the enzyme to be used under non-physiological conditions, and the use of a variety of methods to immobilize or otherwise contain the enzyme, and allow it to be used for extended periods of time. Such immobilization or other containment methods also allow simple and efficient recovery of the desired product of the reaction from the enzyme system. A further advantage of using isolated enzymes in a cell-free system is that multiple enzymes can be used, allowing a series of reactions to be performed.

Micro-organisms containing useful oxidoreductases are widely known in nature and can be found quickly by simple screening (A. Zaks et al, Tetrahedron (2004) 60, 789-797). If a particular oxidoreductase enzyme is required, the enzyme can be readily cloned and over-expressed in a standard industrially useful host such as *S. cerevisiae* or *E. coli*, and isolated by standard methods, and used in an in vitro system.

However, the reducing equivalents must still be provided to such in vitro systems. Analogous to in vivo systems, a sacrificial substrate can be provided, which is oxidized. This generates the necessary reduced state of the nicotinamide adenine dinucleotide cofactors for providing reducing equivalents for the desired reaction.

It will be clear that the need of a sacrificial substrate removes at least some of the advantages of an in vivo system, since a second product, the product of the oxidation of the sacrificial substrate, must now be separated from the desired product. While formate may be used sacrificial substrate, generating $CO_2$ as the result, this requires the use of an additional enzyme, formate dehydrogenase, which may not be convenient.

Thus it is most desirable to provide the electrons required for the reaction, that is, the reducing equivalents required by the oxidoreductase enzyme, in a manner that does not require sacrificial substrates or additional enzymes.

If electrons could be provided from an external source, that is, an electrical current, then the need to provide a sacrificial substrate to provide electrons would be eliminated, and oxidoreductase enzymes could be used as conventional catalysts, performing reactions without the need for living cells or associated enzyme systems or processes.

This situation has been recognized by others, and a number of attempts to deliver electrons to biological systems by electrochemical methods have been published.

It has been reported by Park and Zeikus in *J. Bacteriol.* 181:2403-2410, 1999 that the compound called Neutral Red would undergo reversible chemical oxidoreductions with the nicotinamide adenine dinucleotide cofactor, that is, Neutral Red in its reduced form ($NR_{red}$) has a sufficiently low redox value that it will transfer electrons to, and thus reduce, the nicotinamide adenine dinucleotide cofactor from its oxidized state to its reduced state. In this process, the Neutral Red becomes oxidized to the species $NR_{ox}$ which is then available to accept an electron from the cathode and thus return to the reduced form $NR_{red}$, which is in turn available to again reduce the oxidized state of the nicotinamide adenine dinucleotide cofactor.

U.S. Pat. No. 7,250,288 B2 to Zeikus et al. discusses the need for improving electrode efficiencies in electrochemical bioreactor system and proposes improvements such as linking the nicotinamide adenine dinucleotide cofactor, Neutral Red, and the enzyme fumarate reductase to the electrode in order to improve electron transfer characteristics. While the above may improve electron transfer characteristics, it may also be advantageous to improve upon the electrochemical bioreactor system design and its use in other ways such as those described below.

The requirements for providing reducing equivalents by electrochemical methods are disclosed in PCT publication No. WO2014039767 A1, "Electrochemical Bioreactor Module and Methods of Using the Same". The use of isolated enzymes in conjunction with the electrochemical reduction of the oxidized form of nicotinamide adenine dinucleotide cofactor to its reduced form, and considerations to be made, are disclosed in PCT publication No. WO2016070168 A1, "Improved Electrochemical Bioreactor Module and Use Thereof".

When the oxidized state of the nicotinamide adenine dinucleotide cofactor is electrochemically reduced, several different reduced species can result. These species differ only in the position on the nicotinamide ring at which the reduction has formally occurred. This can be at the 2-position, the 4-position or the 6-position on the nicotinamide ring, and these species are termed the 1,2-dihydro-NAD, 1,4-dihydro-NAD and 1,6-dihydro-NAD isomers respectively. (Chakraverty et al, Biochem. Biophys. Res Comm., (1964), 15(3), 262-268; Chakreverty et al, Jour. Biol. Chem (1969), 244(15), 4208-4217). These are shown below in Illustration A. The carbon atoms of the nicotinamide ring are numbered in the oxidized form, with the nitrogen atom as position 1. The desired reduced product is the 1,4-dihydro-NAD isomer, commonly called β-NADH, and this is the biologically active form of the co-factor required for most dehydrogenase, ketoreductase and P450 enzymes. The other isomers, 1,2-dihydro-NAD and 1,6-dihydro-NAD do not have known useful biological activity with dehydrogenase, ketoreductase or P450 enzymes.

A fourth species, a dimer of the NAD cofactor, can also form during the electrochemical reduction of the oxidized state of nicotinamide adenine dinucleotide. This is termed the 4,4'-dimer and is also shown in Illustration A. Like the 1,2-dihydro-NAD and 1,6-dihydro-NAD forms of the cofactor, the dimer has no known useful biological activity with respect to oxidoreductase enzymes, and cannot deliver reducing equivalents to them (Burnett et al, Biochem. (1968), 10(7), 3328-3333; Biellmann et al, Tetrahedron Letters (1978) 7, 683-686; Kirkor et al, Eur. J. Biochem. (2000), 267, 5014-5022).

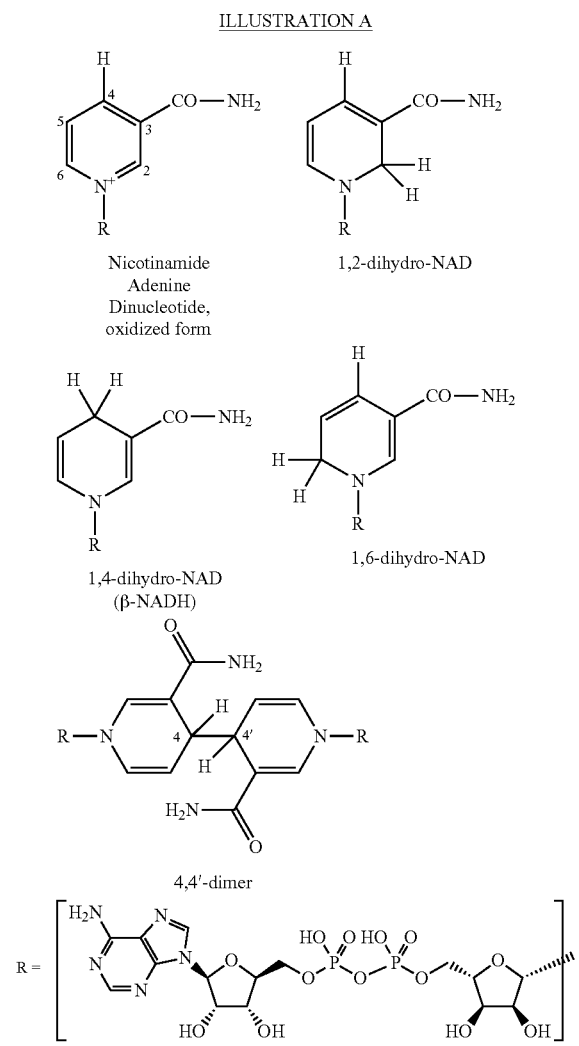

ILLUSTRATION A

In a system where an initial amount of the oxidized state of the nicotinamide adenine dinucleotide cofactor is electrochemically reduced for the purpose of providing reducing equivalents to an oxidoreductase enzyme, the desired, biologically active 1,4-dihydro-NAD isomer will be formed and will provide reducing equivalents to the oxidoreductase enzyme (or enzymes) in the system, and be oxidized back to the oxidized nicotinamide adenine dinucleotide cofactor, ready for another cycle of electrochemical reduction. However, the two non-biologically active isomers, the 1,2-dihydro-NAD and the 1,6-dihydro-NAD, as well as the 4,4'-dimer initially produced by the electrochemical reduction of the oxidized nicotinamide adenine dinucleotide cofactor will not be consumed and will simply remain in the system. The oxidized nicotinamide adenine dinucleotide cofactor resulting from the productive delivery of reducing equivalents to the oxidoreductase enzyme will be again reduced to give a mixture of the three isomers, plus the dimer, as in the previous reduction process. In this cyclic manner, the amount of oxidized nicotinamide adenine dinucleotide cofactor available for electrochemical reduction decreases continually, and after a short period of time, essentially none is left. This problem was recognized four decades ago (Whitesides et al, Appl. Biochem. and Biotech. (1987) 14, 147-197; Whitesides et al, Biotechnology and Genetic Engineering Reviews, Vol. 6. September 1988).

Thus, it is useful to remove the undesired 1,2-dihydro-NAD and the 1,6-dihydro-NAD isomers as well as the 4,4'-dimer should they be produced during the electrochemical reduction of oxidized nicotinamide adenine dinucleotide cofactor to the desired 1,4-dihydro-NAD species, (i.e. β-NADH). Further, it is useful to recover the 1,2-dihydro-NAD and the 1,6-dihydro-NAD isomers as either as the desired 1,4-dihdro-NAD isomer, or as the initial oxidized state of the nicotinamide adenine dinucleotide cofactor.

Provided herein are methods and systems for achieving the above objectives. Other objectives, features, and advantages of the present disclosure will be apparent on review of the specification and claims.

SUMMARY

The present disclosure, in one aspect, provides a system for electrochemically generating $NAD(P)H_2$ reducing equivalents, the system comprising:
  (a) an electrochemical cell comprising an anode contained in an anode chamber and a cathode contained in a cathode chamber;
  (b) a first process stream containing NAD(P), passing through the cathode chamber and continuously in contact with the cathode from which electrons are transferred to the NAD(P) to produce a second process stream containing reduced species 1,4-$NAD(P)H_2$, 1,2-$NAD(P)H_2$, 1,6-$NAD(P)H_2$, and $[NAD(P)]_2$, while optionally producing hydrogen;
  (c) a substrate of an oxidoreductase or P450 enzyme, which, when contacted with the second process stream in the presence of the oxidoreductase or P450 enzyme, is transformed to a product while concomitantly consuming the 1,4-$NAD(P)H_2$ in the second process stream and producing a first recovered NAD(P) and a third process stream; and
  (d) at least one of a renalase enzyme, a Mung Bean Phenol Oxidase enzyme and illumination at a wavelength of about 254 nm or exceeding about 320 nm, which, when contacted with the third process stream, convert at least one of the 1,2-$NAD(P)H_2$, 1,6-$NAD(P)H_2$, and $[NAD(P)]_2$ therein to a second and optionally a third recovered NAD(P).

In some embodiments, the system includes the renalase enzyme for converting the 1,2-$NAD(P)H_2$ and 1,6-$NAD(P)H_2$ into the second recovered NAD(P).

In some embodiments, the system includes the Mung Bean Phenol Oxidase enzyme for converting the 1,2-$NAD(P)H_2$, 1,6-$NAD(P)H_2$, and/or $[NAD(P)]_2$ into the second recovered NAD(P) and/or the third recovered NAD(P).

In some embodiments, the system includes the illumination for converting the $[NAD(P)]_2$ into NAD(P).

In some embodiments, the system includes the renalase enzyme and the Mung Bean Phenol Oxidase enzyme. For example, the third process stream can be contacted with the renalase enzyme resulting in conversion of the 1,2-$NAD(P)H_2$ and 1,6-$NAD(P)H_2$ into the second recovered NAD(P) and a fourth process stream, wherein the fourth process stream can be contacted with the Mung Bean Phenol Oxidase enzyme to convert the $[NAD(P)]_2$ therein to the third recovered NAD(P).

In some embodiments, the system includes the renalase enzyme and the illumination. For example, the third process stream can be contacted with the renalase enzyme resulting in conversion of the 1,2-$NAD(P)H_2$ and 1,6-$NAD(P)H_2$ into the second recovered NAD(P) and a fourth process stream, wherein the fourth process stream can be contacted with the illumination to convert the $[NAD(P)]_2$ therein to the third recovered NAD(P).

In some embodiments, the system includes the Mung Bean Phenol Oxidase enzyme and the illumination. For example, the third process stream can be contacted with the Mung Bean Phenol Oxidase enzyme resulting in conversion of the 1,2-$NAD(P)H_2$ and 1,6-$NAD(P)H_2$ into the second recovered NAD(P) and a fourth process stream, wherein the fourth process stream can be contacted with the illumination to convert the $[NAD(P)]_2$ therein to the third recovered NAD(P).

In some embodiments, the system can include, in one or more of the process streams, an electron transfer mediator (ETM) capable of transferring electrons to NAD(P). The system can also include catalase for decomposing hydrogen peroxide produced by the renalase enzyme, the Mung Bean Phenol Oxidase enzyme, and/or the illumination.

Another aspect relates to a method for electrochemically generating $NAD(P)H_2$ reducing equivalents, the method comprising:
  (a) providing an electrochemical cell comprising an anode contained in an anode chamber and a cathode contained in a cathode chamber;
  (b) passing through the cathode chamber a first process stream which contains NAD(P) and is continuously in contact with the cathode from which electrons are transferred to the NAD(P) to produce a second process stream containing reduced species 1,4-$NAD(P)H_2$, 1,2-$NAD(P)H_2$, 1,6-$NAD(P)H_2$, and $[NAD(P)]_2$, while optionally producing hydrogen;
  (c) contacting the second process stream with a substrate of an oxidoreductase or P450 enzyme such that the substrate, in the presence of the oxidoreductase or P450 enzyme, is transformed to a product while concomitantly consuming the 1,4-$NAD(P)H_2$ in the second process stream and producing a first recovered NAD(P) and a third process stream; and
  (d) contacting the third process stream with at least one of a renalase enzyme, a Mung Bean Phenol Oxidase enzyme and illumination at a wavelength of about 254 nm or exceeding about 320 nm, thereby converting at least one of the 1,2-$NAD(P)H_2$, 1,6-$NAD(P)H_2$, and $[NAD(P)]_2$ therein to a second recovered NAD(P) and optionally a third recovered NAD(P).

The method in some embodiments can further include contacting the third process stream with the renalase enzyme for converting the 1,2-$NAD(P)H_2$ and 1,6-$NAD(P)H_2$ into the second recovered NAD(P).

In some embodiments, the method can further include contacting the third process stream with the Mung Bean Phenol Oxidase enzyme for converting the 1,2-$NAD(P)H_2$, 1,6-$NAD(P)H_2$, and/or $[NAD(P)]_2$ into the second recovered NAD(P) and/or the third recovered NAD(P).

In some embodiments, the method can further include contacting the third process stream with the illumination for converting the $[NAD(P)]_2$ into NAD(P).

In some embodiments, the method can further include contacting the third process stream with the renalase enzyme resulting in conversion of the 1,2-NAD(P)H$_2$ and 1,6-NAD(P)H$_2$ therein into the second recovered NAD(P) and a fourth process stream, and further comprising contacting the fourth process stream with the Mung Bean Phenol Oxidase enzyme to convert the [NAD(P)]$_2$ therein to the third recovered NAD(P).

In some embodiments, the method can further include contacting the third process stream with the renalase enzyme resulting in conversion of the 1,2-NAD(P)H$_2$ and 1,6-NAD(P)H$_2$ therein into the second recovered NAD(P) and a fourth process stream, and further comprising contacting the fourth process stream with the illumination to convert the [NAD(P)]$_2$ therein to the third recovered NAD(P).

In some embodiments, the method can further include contacting the third process stream with the Mung Bean Phenol Oxidase enzyme resulting in conversion of the 1,2-NAD(P)H$_2$ and 1,6-NAD(P)H$_2$ therein into the second recovered NAD(P) and a fourth process stream, and further comprising contacting the fourth process stream with the illumination to convert the [NAD(P)]$_2$ therein to the third recovered NAD(P).

In some embodiments, the method can further include providing, in one or more of the process streams, an electron transfer mediator (ETM) capable of transferring electrons to NAD(P).

In some embodiments, the method can further include providing catalase for decomposing hydrogen peroxide produced by the renalase enzyme, the Mung Bean Phenol Oxidase enzyme, and/or the illumination.

In some embodiments, the method can further include returning the third process stream to the cathode chamber.

In any of the systems and methods disclosed herein, the renalase enzyme and/or Mung Bean Phenol Oxidase enzyme may be recombinantly expressed from microorganisms such as *Escherichia coli, Bacillus subtilis, Corynebacterium glutamicum, Saccharomyces cerevisiae, Pichia pastoris*, and *Bacillus megaterium*.

The renalase enzyme in certain embodiments can be a mutant form (naturally occurring or genetically engineered) having a lower oxidation activity for 1,4-NAD(P)H$_2$ than the wild type renalase enzyme, and/or a higher oxidation activity for 1,2-NAD(P)H$_2$ and 1,6-NAD(P)H$_2$ than the wild type renalase enzyme. In some examples, the mutant form can be recombinantly expressed from microorganisms such as *Escherichia coli, Bacillus subtilis, Corynebacterium glutamicum, Saccharomyces cerevisiae, Pichia pastoris*, and *Bacillus megaterium*.

The Mung Bean Phenol Oxidase enzyme can be a mutant form (naturally occurring or genetically engineered) having a lower oxidation activity for 1,4-NAD(P)H$_2$ than the wild type Mung Bean Phenol Oxidase enzyme, and/or a higher oxidation activity for 1,2-NAD(P)H$_2$, 1,6-NAD(P)H$_2$ and/or [NAD(P)]$_2$ than the wild type Mung Bean Phenol Oxidase enzyme. In some embodiments, the mutant form is recombinantly expressed from microorganisms such as *Escherichia coli, Bacillus subtilis, Corynebacterium glutamicum, Saccharomyces cerevisiae, Pichia pastoris*, and *Bacillus megaterium*.

Also provided herein is a process for providing electrochemically generated reducing power via the reduction of an oxidized form of phosphorylated or non-phosphorylated forms of nicotinamide adenine dinucleotide cofactor to a redox enzyme system for the purpose of catalyzing a transformation of a substrate molecule.

The process can include steps for preventing the loss of cofactor material to reduced forms that are not used by the redox enzyme system for the purpose of catalyzing a transformation of a substrate molecule.

The process can include the electrochemical reduction of the oxidized state of nicotinamide adenine dinucleotide cofactor to give a mixture of the desired 1,4-dihydro-NAD species with the undesired 1,2-dihydro-NAD and 1,6-dihydro-NAD species, and the undesired 4,4'-dimer. The desired 1,4-dihydro-NAD species is converted back to the oxidized form of the nicotinamide adenine dinucleotide cofactor in the course of providing reducing equivalents to the oxidoreductase enzyme which is present to catalyze the transformation of the substrate molecule. The remaining mixture of the 1,2-dihydro-NAD and 1,6-dihydro-NAD species, the 4,4'-dimer, together with the oxidized state of the nicotinamide adenine dinucleotide cofactor is acted upon by the renalase enzyme. This enzyme oxidizes the 1,2-dihydro-NAD and 1,6-dihydro-NAD species back to the oxidized state of the nicotinamide adenine dinucleotide cofactor in the presence of oxygen, producing hydrogen peroxide in the process. The Mung Bean enzyme oxidizes the 4,4'-dimer back to two molecules of the oxidized state of the nicotinamide adenine dinucleotide cofactor, also by using oxygen and generating hydrogen peroxide. Thus all species originally produced by the electrochemical reduction of the oxidized form of the nicotinamide adenine dinucleotide cofactor, both desired and undesired, are returned to the original oxidized state of the nicotinamide adenine dinucleotide cofactor and no cofactor material is lost. The 4,4'-dimer is photo-active, and can be returned to the oxidized state of the nicotinamide adenine dinucleotide cofactor species by irradiation with the appropriate wavelength; this may be performed in place of, or in conjunction with, the Mung Bean oxidase.

BRIEF DESCRIPTION OF THE DRAWINGS

FIG. 1 illustrates, in a schematic, the utilization of renalase, Mung Bean Phenol Oxidase, and optionally illumination to recover and recycle cofactor material from the mixture of the desired 1,4-dihydro-NAD species plus the undesired 1,2-dihydro-NAD and 1,6-dihydro-NAD species and the undesired 4,4'-dimer which are formed via the electrochemical reduction of the oxidized state of nicotinamide adenine dinucleotide cofactor. In FIG. 1, the 1,2-dihydro-NAD, 1,4-dihydro-NAD and the 1,6-dihydro-NAD species of the nictotinamide adenine dinucleotide cofactor are named 1,2-NAD(P)H$_2$, 1,4-NAD(P)H$_2$ and 1,6-NAD(P)H$_2$ respectively, while the 4,4'-dimer is named [NAD(P)]$_2$ and the oxidized form is named NAD(P).

DETAILED DESCRIPTION

The current literature most commonly uses the descriptor "NAD(P)+" to indicate the oxidized state of the phosphorylated and non-phosphorylated forms of the nicotinamide adenine dinucleotide, and "NAD(P)H" to indicate the reduced state. The reduced state of the phosphorylated and non-phosphorylated forms of the nicotinamide adenine dinucleotide are produced by adding two electrons and two protons to the oxidized state. This common nomenclature is misleading, as plain reading of the common descriptors "NAD(P)+" and "NAD(P)H" show the oxidized state of the phosphorylated and non-phosphorylated forms of the nicotinamide adenine dinucleotide to be a positively charged species "NAD(P)+", while the reduced state of the phosphorylated and non-phosphorylated forms of the nicotinamide adenine dinucleotide, "NAD(P)H", is shown to have only one hydrogen added relative to the oxidized state. Neither of these representations is true. The oxidized state of the phosphorylated and non-phosphorylated forms of the nicotinamide adenine dinucleotide is a neutral molecule in which the nitrogen of the nicotinamide ring bears a formal positive charge with is balanced by a negative charge one of the deprotonated phosphate linkages, thus forming an internal salt or zwitterion. The reduced state of the phosphorylated and non-phosphorylated forms of the nicotinamide adenine dinucleotide has formally accepted a hydrogen molecule, $H_2$, relative to the oxidized state, and this achieved by two one-electron transfers balanced by two protons. This is shown formally by the following balanced chemical reaction:

$$NAD(P) + 2H^+ + 2e^- \rightarrow NAD(P)H_2$$

The published molecular weights of the oxidized and reduced states of the non-phosphorylated form of the nicotinamide adenine dinucleotide indicate the reality of this reaction clearly, the molecular weights being 663.43 Da and 665.44 Da respectively and the difference being the molecular weight of a single hydrogen molecule, $H_2$.

In the present disclosure, the descriptor "NAD(P)" indicates the oxidized state of the phosphorylated and non-phosphorylated forms of the nicotinamide adenine dinucleotide, while the descriptor "NAD(P)$H_2$" indicates the reduced state of the phosphorylated and non-phosphorylated forms of the nicotinamide adenine dinucleotide. Further, the descriptors "1,2-NAD(P)$H_2$", "1,4-NAD(P)$H_2$" and "1,6-NAD(P)$H_2$" are used to indicate the three stereoisomers of the nicotinamide ring that can occur upon reduction of NAD(P), in which a hydrogen molecule has been formally added across the 1,2-, 1,4- and 1,6-positions of the nicotinamide ring. It will be clear to those skilled in the art that 1,4-NAD(P)$H_2$ is commonly called β-NADH, and is the stereoisomer of the reduced state of the phosphorylated and non-phosphorylated forms of nicotinamide adenine dinucleotide which is active with oxidoreductase and P450 enzymes.

In the present disclosure, the 4,4'-dimer that is also known to form as a consequence of a one-electron transfer to NAD(P) is indicated by the descriptor "[NAD(P)]$_2$".

The present disclosure, in some embodiments, is directed to an improved version and improved use of the "Electrochemical Bioreactor Module" (EBM) previously described in PCT Patent Application Publication Nos. WO2014039767 A1 and WO2016070168 A1, which are incorporated herein by reference in its entirety.

An EBM can include one or more of the following components:
a. an anode contained in an anode chamber and a cathode contained in a cathode chamber;
b. deionized water in the anode chamber in contact with the anode;
c. a proton permeable membrane that separates the anode and cathode chambers;
d. a liquid phase in the cathode chamber continuously in contact with the cathode, said liquid phase optionally comprising an electron transfer mediator (ETM) capable of transferring reducing equivalents to a redox enzyme system, said redox enzyme system comprising a redox enzyme and a cofactor;
e. a process stream containing a substrate to be transformed via catalysis by the redox enzyme system into a desired product;
f. a membrane located between the cathode and the process stream, said membrane capable of preventing the optional ETM and the redox enzyme system from significantly entering into the process stream; and
g. an external power source providing a voltage between the anode and the cathode.

In certain embodiments, an improved EBM or process using the EBM of the present disclosure can include the enzyme renalase, the Mung Bean Phenol Oxidase, and illumination to recover the undesired forms of cofactor that result from electrochemical reduction of NAD(P).

The enzyme renalase (Moran et al, J. Am. Chem. Soc. (2013), 135, 13980-13987; Moran, G. R., Biochimica et Biophysica Acta 1864 (2016) 177-186), is capable of oxidizing the 1,2-dihydro-NAD and 1,6-dihydro-NAD species back to the oxidized state of the nicotinamide adenine dinucleotide cofactor.

Another enzyme isolated from Mung Bean and currently termed "Mung Bean Phenol Oxidase" (Fricks et al, Arch. Biochem. Biophys., (1973)169, 837-841). This enzyme oxidizes the 4,4'-dimer, [NAD(P)]$_2$, that can be formed under electrochemically reducing conditions back to the oxidized state of nicotinamide adenine dinucleotide. This enzyme has also been reported as having the same activity as renalase and being able to oxidize the 1,2-NAD(P)$H_2$ and 1,6-NAD(P)$H_2$ species back to the oxidized state of nicotinamide adenine dinucleotide as well (Kono et al, Bull. Agr. Chem. Soc. Japan, (1958) 22(6) 404-410).

It has also recently been shown that illumination of electrochemically prepared 4,4'-dimer at about 254 nm or at wavelengths exceeding 320 nm leads to regeneration of the oxidized state of nicotinamide adenine dinucleotide. (Czochralska et al, (1980) Arch. Biochem. Biophys. 199, 497; Czochralska et al, (1990) Photochem. Photobiol. 51, 401-410).

Thus it is useful to incorporate the renalase and Mung Bean Phenol Oxidase enzymes, and the illumination of the [NAD(P)]$_2$ dimer of nicotinamide adenine dinucleotide in a process for the recovery of cofactor material, and for the prevention of the loss of cofactor material to forms which are not used by oxidoreductase enzymes such as dehydrogenases, ketoreductases or P450 enzymes.

In one embodiment, the present disclosure provides a process that comprises:
a) a process stream containing NAD(P) which is passed through the cathode chamber of an electrochemical cell such that the desired, biologically active 1,4-NAD(P)H$_2$ is produced, together with the undesired 1,2-NAD(P)H$_2$, 1,6-NAD(P)H$_2$ and [NAD(P)]$_2$ species;
b) providing a substrate molecule that is to be transformed via the catalytic reaction of an oxidoreductase enzyme, such as a dehydrogenase or ketoreductase, or a P450 enzyme, to produce a desired product molecule;
c) contacting the process stream containing both the desired and undesired cofactor species with an oxidoreductase, such as a dehydrogenase or ketoreductase, or a P450 enzyme, capable of using the reducing equivalents presented by the 1,4-NAD(P)H$_2$ to perform a desired reaction in which a substrate molecule is transformed to a desired product molecule, while the 1,4-NAD(P)H$_2$ is concomitantly transformed back to NAD(P);
d) recovering the cofactor material from the undesired, leaving the undesired 1,2-NAD(P)H$_2$ and 1,6-NAD(P)H$_2$ cofactor species present in the process stream by contacting the process stream with the renalase enzyme in the presence of oxygen for a sufficient time that the renalase enzyme can catalyze the oxidation of the undesired 1,2-NAD(P)H$_2$ and 1,6-NAD(P)H$_2$ species that may be present in the process stream to the oxidized form of the cofactor, NAD(P);

e) recovering the cofactor material from the undesired and [NAD(P)]$_2$ species present in the process stream by contacting the process stream with Mung Bean Phenol Oxidase in the presence of oxygen for a sufficient time that the Mung Bean Phenol Oxidase enzyme can catalyze the oxidation and any [NAD(P)]$_2$ present in the process stream to the oxidized form of the cofactor NAD(P);

f) returning the process stream now containing all of the original nicotinamide adenine dinucleotide as the oxidized form NAD(P) to the cathode chamber of the electrochemical cell for reduction.

In one embodiment, a process stream containing NAD(P) is passed through the cathode chamber of the electrochemical cell such that 1,2-NAD(P)H$_2$, 1,4-NAD(P)H$_2$, 1,6-NAD(P)H$_2$ and the 4,4'-dimer, [NAD(P)]$_2$ are produced. The process stream containing the mixture of NAD(P)H$_2$ species is then contacted with an oxidoreductase enzyme (e.g. a dehydrogenase, ketoreductase, or P450 enzyme) capable of using the reducing equivalents from the 1,4-NAD(P)H$_2$ to perform a desired reaction in which a substrate molecule is transformed to a desired product molecule, while the 1,4-NAD(P)H$_2$ is concomitantly transformed back to NAD(P). The enzyme utilizing the 1,4-NAD(P)H$_2$ may be present in the process stream, immobilized on beads or other suitable material and held in a packed column, or contained by a membrane as described in PCT Patent Application Publication No. WO2016070168 A1, which is incorporated herein by reference in its entirety.

The process stream, after contacting the oxidoreductase enzyme and after the 1,4-NAD(P)H$_2$ has been transformed back to NAD(P), is then contacted with the renalase enzyme. In the presence of oxygen, the renalase enzyme oxidizes the undesired 1,2-NAD(P)H$_2$ and 1,6-NAD(P)H$_2$ species that may be present back to NAD(P) with the concomitant production of hydrogen peroxide. An enzyme such as catalase, or a suitable inorganic catalyst (e.g. MnO$_2$), may be present to decompose the hydrogen peroxide and thus prevent deleterious effects by the hydrogen peroxide.

The renalase enzyme may be immobilized on beads or a suitable support, immobilized on, or contained by, a membrane or kept from freely circulating in the process stream by other standard methods known to those skilled in the art of enzymatic reactions. As the renalase enzyme has some activity towards the desirable 1,4-NAD(P)H$_2$ species and will oxidize this back to NAD(P), it is better if the renalase enzyme is not freely circulating in the process stream, and that the process stream is contacted with the renalase after the 1,4-NAD(P)H$_2$ present in the process stream has been consumed by the oxidoreductase enzyme, and has been used to perform a useful reaction on a substrate.

The process stream is then brought into contact with the Mung Bean Phenol oxidase in the presence of oxygen and any undesired 4,4'-dimer, [NAD(P)]$_2$, present is thus oxidized back to NAD(P) with the concomitant production of hydrogen peroxide. The Mung Bean Phenol Oxidase may be immobilized on beads or a suitable support, immobilized on, or contained by, a membrane or kept from freely circulating in the process stream by other standard methods known to those skilled in the art of enzymatic reactions. As the Mung Bean Phenol Oxidase enzyme has some activity towards the desirable 1,4-NAD(P)H$_2$ species and will oxidize this back to NAD(P), it is better if the Mung Bean Phenol Oxidase enzyme is not freely circulating in the process stream, and that the process stream is contacted with the Mung Bean Phenol Oxidase after the desirable 1,4-NAD(P)H$_2$ present in the process stream has been consumed by the oxidoreductase enzyme.

In another embodiment, the process stream, after contacting the oxidoreductase enzyme, may be contacted first with the Mung Bean Phenol Oxidase enzyme for oxidation of the undesired [NAD(P)]$_2$ back to NAD(P), and then subsequently with the renalase enzyme for oxidation of the undesired 1,2-NAD(P)H$_2$ and 1,6-NAD(P)H$_2$ species back to NAD(P).

In another embodiment, the process stream, after contacting the oxidoreductase enzyme may be contacted with the renalase enzyme and subsequently irradiated with light at 254 nm or at wavelengths exceeding 320 nm for decomposing the undesired [NAD(P)]$_2$ dimer back to NAD(P).

In another embodiment, the process stream, after contacting the oxidoreductase enzyme, may be contacted not only with the Mung Bean Phenol Oxidase enzyme for oxidation of the undesired [NAD(P)]$_2$ dimer back to NAD(P), and also for oxidation of the undesired 1,2-NAD(P)H$_2$ and 1,6-NAD(P)H$_2$ species to NAD(P) as the Mung Bean Phenol Oxidase enzyme is known to have activity for the oxidation of the undesired 1,2-NAD(P)H$_2$ and 1,6-NAD(P)H$_2$ species back to NAD(P).

It will be clear to those skilled in the art that the order of the steps in the process for recovering cofactor material as NAD(P) from the undesired 1,2-NAD(P)H$_2$, 1,6-NAD(P)H$_2$, and [NAD(P)]$_2$ species by the above described steps of contacting the process stream with renalase, Mung Bean Phenol Oxidase or illuminating it with light at 254 nm or at wavelengths exceeding 320 nm may be done in any order or combination.

It will be clear to those skilled in the art that the Mung Bean Phenol Oxidase and the renalase enzymes may be engineered by known methods to allow greater stability and therefore lifetime in the process, or to allow greater activity, or to allow increased ease and efficiency of immobilization, or to allow the more efficient expression and isolation of these enzymes.

It will be equally clear to those skilled in the art of enzymatic reactions that the Mung Bean Phenol Oxidase enzyme may be engineered to allow increased activity for the oxidation of the undesired 1,2-NAD(P)H$_2$ and 1,6-NAD(P)H$_2$, species to NAD(P), in addition to its activity for oxidizing the undesired [NAD(P)]$_2$ dimer to NAD(P).

In certain embodiments, the renalase enzyme and the Mung Bean Phenol Oxidase enzyme may be engineered to have insignificant (e.g., lower than wide-type) activity on the desirable 1,4-NAD(P)H$_2$ species, but useful (e.g., higher than wide-type) activity on the undesired 1,2-NAD(P)H$_2$, 1,6-NAD(P)H$_2$, and [NAD(P)]$_2$ species resulting from the electrochemical reduction of NAD(P). These enzymes may then be circulated with the process stream, or the enzymes may be immobilized or otherwise contained and contacted with the process stream in any order that is convenient, including prior to contacting the process stream with the oxidoreductase or P450 enzyme which is acting upon the provided substrate.

EXAMPLES

Example I

This example describes an exemplary process in which the undesired 1,2-NAD(P)H$_2$ and 1,6-NAD(P)H$_2$ isomers are re-oxidized to NAD(P) by renalase, and the undesired [NAD(P)]$_2$ dimer is oxidatively cleaved to NAD(P) by Mung Bean Phenol Oxidase.

To demonstrate the process described in the present disclosure, Mung Bean Phenol Oxidase is extracted from Mung Bean seedlings as described by Burnett and Underwood (Biochem. 7(10), 3328-3333, 1968). The gene human renalase isoform 1 is cloned onto a plasmid for expression in E. coli, including codon optimization. The sequence of the renalase is revealed by Pandini et al. (Protein Expression and Purification 72 (2010) 244-253). The enzyme is expressed as an inclusion body, the inclusion bodies collected and refolded as described by Padini et al (Protein Expression and Purification 72 (2010) 244-253). The renalase enzyme (MW=35 KDa) is held in a container in which an inlet and an outlet are provided, with a permeable membrane between the inlet and the outlet that is of a sufficiently low molecular weight cutoff to prevent the renalase from passing through it, but also having a sufficiently high molecular weight cutoff that all species of the nicotinamide adenine dinucleotide present in the process stream can pass through it. A membrane with a molecular weight cutoff of 10 KDa is used. In a similar manner, the Mung Bean Phenol Oxidase enzyme is held in a separate container with an inlet and an outlet and that also includes a membrane between the inlet and the outlet that is permeable, having a sufficiently low molecular weight cutoff that the Mung Bean Phenol Oxidase cannot pass through it, but a sufficiently high molecular weight cutoff that all species of the nicotinamide adenine dinucleotide present in the process stream can pass through it. A membrane with a molecular weight cutoff of 10 KDa is used. To allow the use of an oxidoreductase enzyme that demonstrates the presence of useful amounts of the desired 1,4-NAD(P)H$_2$ cofactor, the membrane system described in published PCT Patent Application WO2016070168 A1 published 6 May 2016, and which is also described in U.S. Pat. Nos. 4,705,704 and 5,077,217 for the purpose of containing an enzyme. The enzyme Horse Liver Alcohol Dehydrogenase is used, with cyclohexanone or benzaldehyde used as the substrate for the alcohol dehydrogenase enzyme. A process stream containing 1 to 2 mM of NAD(P) is prepared and buffered to a pH suitable for all three enzymes; a pH of 7.5 is used. The process stream containing the NAD(P) is pumped through the cathode chamber of the electrochemical cell, which is energized at approximately 2 volts, and the NAD(P) cofactor is reduced to give the desired 1,4-NAD(P)H$_2$ form of the cofactor, and also the undesired 1,2-NAD(P)H$_2$, 1,6-NAD(P)H$_2$ and 4,4'-dimer, [NAD(P)]$_2$ forms of the cofactor. Exiting the cathode chamber, the NAD(P) process stream goes through the membrane system containing the alcohol dehydrogenase, where the desired 1,4-NAD(P)H$_2$ form of the cofactor provides reducing equivalents to the alcohol dehydrogenase, the cyclohexanone or benzaldehyde substrate is reduced to cyclohexanol or benzyl alcohol product respectively, thus consuming the 1,4-NAD(P)H$_2$ form of the cofactor and producing the oxidized form NAD(P). The process stream then proceeds to the inlet of the container holding the renalase enzyme. The process stream mixes with the renalase enzyme and the renalase enzyme oxidizes the undesired 1,2-NAD(P)H$_2$ and 1,6-NAD(P)H$_2$ forms of the cofactor to NAD(P). The process stream then passes through the membrane but the renalase enzyme is held in its container by the membrane. After passing through the membrane the process stream proceeds to the outlet of the container holding the renalase enzyme. From here the process stream passes to the inlet of the container holding the Mung Bean Phenol Oxidase enzyme. The process stream mixes with the Mung Bean Phenol Oxidase enzyme and the enzyme oxidizes the undesired 4,4'dimer, [NAD(P)]$_2$ form of the cofactor to NAD(P). The process stream then passes through the membrane but the Mung Bean Phenol Oxidase enzyme is held in its container by the membrane. The process stream exits through the outlet of the container holding the Mung Bean Phenol Oxidase enzyme, and now contains only NAD(P) as the other forms of the cofactor have all been oxidized by the alcohol dehydrogenase, the renalase and the Mung Bean Phenol Oxidase enzymes. The process stream is returned to the pump, and sent into the cathode chamber to repeat the cycle.

Example II

This example describes an exemplary process in which the undesired 1,2-NAD(P)H$_2$ and 1,6-NAD(P)H$_2$ isomers are re-oxidized to NAD(P) by renalase, and the undesired [NAD(P)]$_2$ dimer is oxidatively cleaved to NAD(P) by illumination with UV light at 254 nm.

The process described in Example I is used, excepting the container holding the Mung Bean Phenol Oxidase is replaced by a quartz tube through which the process stream can flow unimpeded by any membrane. Outside the quartz tube an ultraviolet lamp is present, and illuminates the tube with light at 254 nm which passes through the quartz and photolytically cleaves the 4,4-dimer of the cofactor, [NAD(P)]$_2$, to NAD(P). Upon exiting the quartz tube, the process stream is returned to the pump, and sent into the cathode chamber to repeat the cycle.

Equivalents

The present disclosure provides among other things novel methods and devices for providing reducing equivalents to biological systems. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Incorporation by Reference

All publications, patents and patent applications cited above are incorporated by reference herein in their entirety for all purposes to the same extent as if each individual publication or patent application were specifically indicated to be so incorporated by reference.

The invention claimed is:

1. A system for electrochemically generating NAD(P)H$_2$ reducing equivalents comprising:
 a. an electrochemical cell comprising an anode contained in an anode chamber and a cathode contained in a cathode chamber;
 b. a first process stream containing NAD(P), passing through the cathode chamber and continuously in contact with the cathode from which electrons are transferred to the NAD(P) to produce a second process stream containing reduced species 1,4-NAD(P)H$_2$, 1,2-NAD(P)H$_2$, 1,6-NAD(P)H$_2$, and [NAD(P)]$_2$, while optionally producing hydrogen;
 c. a substrate of an oxidoreductase or P450 enzyme, which, when contacted with the second process stream in the presence of the oxidoreductase or P450 enzyme, is transformed to a product while concomitantly consuming the 1,4-NAD(P)H$_2$ in the second process stream and producing a first recovered NAD(P) and a third process stream; and d. at least one of a renalase enzyme, a Mung Bean Phenol Oxidase enzyme and illumination at a wavelength of about 254 nm or exceeding about 320 nm, which, when contacted with the third process stream, convert at least one of the 1,2-NAD(P)H$_2$, 1,6-NAD(P)H$_2$, and [NAD(P)]$_2$ therein to a second and optionally a third recovered NAD(P).

2. The system of claim 1, comprising the renalase enzyme for converting the 1,2-NAD(P)H$_2$ and 1,6-NAD(P)H$_2$ into the second recovered NAD(P).

3. The system of claim 1, comprising the Mung Bean Phenol Oxidase enzyme for converting the 1,2-NAD(P)H$_2$, 1,6-NAD(P)H$_2$, and/or [NAD(P)]$_2$ into the second recovered NAD(P) and/or the third recovered NAD(P).

4. The system of claim 1, comprising the illumination for converting the [NAD(P)]$_2$ into NAD(P).

5. The system of claim 1, comprising the renalase enzyme and the Mung Bean Phenol Oxidase enzyme.

6. The system of claim 5, wherein the third process stream is contacted with the renalase enzyme resulting in conversion of the 1,2-NAD(P)H$_2$ and 1,6-NAD(P)H$_2$ into the second recovered NAD(P) and a fourth process stream, wherein the fourth process stream is contacted with the Mung Bean Phenol Oxidase enzyme to convert the [NAD(P)]$_2$ therein to the third recovered NAD(P).

7. The system of claim 1, comprising the renalase enzyme and the illumination.

8. The system of claim 7, wherein the third process stream is contacted with the renalase enzyme resulting in conversion of the 1,2-NAD(P)H$_2$ and 1,6-NAD(P)H$_2$ into the second recovered NAD(P) and a fourth process stream, wherein the fourth process stream is contacted with the illumination to convert the [NAD(P)]$_2$ therein to the third recovered NAD(P).

9. The system of claim 1, comprising the Mung Bean Phenol Oxidase enzyme and the illumination.

10. The system of claim 9, wherein the third process stream is contacted with the Mung Bean Phenol Oxidase enzyme resulting in conversion of the 1,2-NAD(P)H$_2$ and 1,6-NAD(P)H$_2$ into the second recovered NAD(P) and a fourth process stream, wherein the fourth process stream is contacted with the illumination to convert the [NAD(P)]$_2$ therein to the third recovered NAD(P).

11. The system of claim 1, further comprising, in one or more of the process streams, an electron transfer mediator (ETM) capable of transferring electrons to NAD(P).

12. The system of claim 1, further comprising catalase for decomposing hydrogen peroxide produced by the renalase enzyme, the Mung Bean Phenol Oxidase enzyme, and/or the illumination.

13. A method for electrochemically generating NAD(P)H$_2$ reducing equivalents comprising:
a. providing an electrochemical cell comprising an anode contained in an anode chamber and a cathode contained in a cathode chamber;
b. passing through the cathode chamber a first process stream which contains NAD(P) and is continuously in contact with the cathode from which electrons are transferred to the NAD(P) to produce a second process stream containing reduced species 1,4-NAD(P)H$_2$, 1,2-NAD(P)H$_2$, 1,6-NAD(P)H$_2$, and [NAD(P)]$_2$, while optionally producing hydrogen;
c. contacting the second process stream with a substrate of an oxidoreductase or P450 enzyme such that the substrate, in the presence of the oxidoreductase or P450 enzyme, is transformed to a product while concomitantly consuming the 1,4-NAD(P)H$_2$ in the second process stream and producing a first recovered NAD(P) and a third process stream; and
d. contacting the third process stream with at least one of a renalase enzyme, a Mung Bean Phenol Oxidase enzyme and illumination at a wavelength of about 254 nm or exceeding about 320 nm, thereby converting at least one of the 1,2-NAD(P)H$_2$, 1,6-NAD(P)H$_2$, and [NAD(P)]$_2$ therein to a second recovered NAD(P) and optionally a third recovered NAD(P).

14. The method of claim 13, further comprising contacting the third process stream with the renalase enzyme for converting the 1,2-NAD(P)H$_2$ and 1,6-NAD(P)H$_2$ into the second recovered NAD(P).

15. The method of claim 13, further comprising contacting the third process stream with the Mung Bean Phenol Oxidase enzyme for converting the 1,2-NAD(P)H$_2$, 1,6-NAD(P)H$_2$, and/or [NAD(P)]$_2$ into the second recovered NAD(P) and/or the third recovered NAD(P).

16. The method of claim 13, further comprising contacting the third process stream with the illumination for converting the [NAD(P)]$_2$ into NAD(P).

17. The method of claim 13, further comprising contacting the third process stream with the renalase enzyme resulting in conversion of the 1,2-NAD(P)H$_2$ and 1,6-NAD(P)H$_2$ therein into the second recovered NAD(P) and a fourth process stream, and further comprising contacting the fourth process stream with the Mung Bean Phenol Oxidase enzyme to convert the [NAD(P)]$_2$ therein to the third recovered NAD(P).

18. The method of claim 13, further comprising contacting the third process stream with the renalase enzyme resulting in conversion of the 1,2-NAD(P)H$_2$ and 1,6-NAD(P)H$_2$ therein into the second recovered NAD(P) and a fourth process stream, and further comprising contacting the fourth process stream with the illumination to convert the [NAD(P)]$_2$ therein to the third recovered NAD(P).

19. The method of claim 13, further comprising contacting the third process stream with the Mung Bean Phenol Oxidase enzyme resulting in conversion of the 1,2-NAD(P)H$_2$ and 1,6-NAD(P)H$_2$ therein into the second recovered NAD(P) and a fourth process stream, and further comprising contacting the fourth process stream with the illumination to convert the [NAD(P)]$_2$ therein to the third recovered NAD(P).

20. The method of claim 13, further comprising providing, in one or more of the process streams, an electron transfer mediator (ETM) capable of transferring electrons to NAD(P), and/or providing catalase for decomposing hydrogen peroxide produced by the renalase enzyme, the Mung Bean Phenol Oxidase enzyme, and/or the illumination.

* * * * *